(12) United States Patent
Kuhn et al.

(10) Patent No.: US 6,640,654 B2
(45) Date of Patent: Nov. 4, 2003

(54) VARIABLE SPLIT SAMPLER FOR AIR MONITORING

(75) Inventors: Kenneth A. Kuhn, Birmingham, AL (US); Donald P. Segers, Homewood, AL (US); Melody L. Thompson, Pelham, AL (US)

(73) Assignee: O.I. Corporation, College Station, TX (US)

(*) Notice: Subject to any disclaimer, the term of this patent is extended or adjusted under 35 U.S.C. 154(b) by 0 days.

(21) Appl. No.: 10/207,288

(22) Filed: Jul. 29, 2002

(65) Prior Publication Data

US 2002/0184957 A1 Dec. 12, 2002

Related U.S. Application Data

(63) Continuation of application No. 09/627,970, filed on Jul. 28, 2000, now abandoned.
(51) Int. Cl.[7] .................................................. G01N 1/00
(52) U.S. Cl. ................................. 73/863.33; 73/864.81
(58) Field of Search ........................ 73/863.01, 863.33, 73/864.34, 864.81, 863.23; 137/624.11, 624.13, 624.15, 624.18, 624.2, 625.11, 625.4, 627, 627.5, 597, 606

(56) References Cited

U.S. PATENT DOCUMENTS

| | | | | |
|---|---|---|---|---|
| 5,469,751 A | * | 11/1995 | Weiss et al. | 73/863.33 |
| 5,824,919 A | * | 10/1998 | Hansen | 73/863.23 |
| 5,900,214 A | * | 5/1999 | Girard et al. | 422/62 |
| 6,022,510 A | * | 2/2000 | Springmann | 422/101 |
| 6,125,710 A | * | 10/2000 | Sharp | 73/863.31 |

* cited by examiner

*Primary Examiner*—Robert Raevis
(74) *Attorney, Agent, or Firm*—Wong, Cabello, Lutsch, Rutherford & Brucculeri, L.L.P.

(57) ABSTRACT

An apparatus for controllably varying the sample volume for each of a plurality of sample lines used with air monitoring equipment is disclosed. The sample volume is varied depending on the compound or compounds of interest sampled through each line. The flow volume from each sample line is determined and controlled by proportional time that an electrically actuated valve is open for that sampling line.

9 Claims, 2 Drawing Sheets

VARIABLE SPLIT SAMPLER FOR AIR MONITORING

This is a continuation of application Ser. No. 09/627,970, filed Jul. 28, 2000, now abandoned.

BACKGROUND OF THE INVENTION

1. Field of the Invention

This invention relates generally to automated air-monitoring equipment used to analyze and determine the concentration of compounds, such as volatile organic compounds, in sampled air. More specifically, the invention relates to an apparatus for sampling air for two or more similar or dissimilar compounds simultaneously at one or more locations, that allows for different sample volume requirements and/or flow restrictions for each sample line.

2. Description of Related Art

Automated air-monitoring equipment typically collects a known volume of air that is analyzed for compounds of interest, including volatile organic compounds and chemical-warfare agents, to determine the concentration (e.g., unit mass per unit volume) of the compound in the sampled air. The air monitor or sampling device may perform direct or indirect concentration measurements. Direct methods include measuring the concentration of the target compound in a static sample of air or dynamically measuring the concentration in a flowing air stream. An indirect method typically involves collecting the compound of interest from an air sample by some means before analysis; this approach is used to pre-concentrate the analyte for low-level detection. For direct and indirect monitoring cases, the volume of the sampled air must be known to determine the concentration of the target compound. For indirect methods, the concentration of the analyte in the sampled air can be back-calculated based on the quantitative analysis of the collected compound and the volume of sampled air.

The air monitor may use a vacuum pump or other means to sample a known volume of air that is subsequently analyzed for the compound of interest. The usual methods to measure the volume of the air sample include collecting the air sample in a fixed, known volume container, or by measuring the sample flow rate and the sampling time, the product of which yields the sample volume.

Air monitors usually perform "point sampling", which means that the air monitor collects an air sample at one particular location. To sample more than one point automatically, the monitor must be designed to collect air samples from multiple locations either simultaneously or sequentially. When "multiple-point sampling" is required, two or more sample lines (i.e., flexible or rigid tubing) are used, and manual or automated devices incorporating pneumatically or electrically controlled valves can be used with vacuum sampling to switch the sampling between the different lines leading to different sampling points. These switching sampling devices, sometimes called "stream-selection" devices or systems, simply alternate sampling between different points.

Automated multiple-point, stream-selection sampling devices that are based on vacuum sampling generally collect equal volumes of air from each of the multiple points by using a fixed sample flow rate and a fixed sampling time at each point. That is, the volume of gas collected is the same for each sampling point because the valve(s) merely switch between lines at predetermined fixed intervals.

In these stream-selection systems, the volume of the air sample for each sampling point equals the volume of air collected while sampling that point. The two sample lines converge at the inlet of the sampling device. The expected concentration of the compound may be different at the different sampling points, the required monitoring level (i.e., target concentration level) may differ for each of the multiple sampling points, or the volumes of air required for the analyses may vary depending on the specific compounds being sampled. Additionally, in some instances dissimilar compounds must be sampled through separate sample lines at the same or different locations. There is no simple, reliable way to handle these differences and variations by controlling the portion of the total volume of air sampled from each sample line.

In theory, variable restrictions could be added to one or more of the sample lines to tune the proportion of sample flow in each line to the desired ratio. However, this approach is impractical because variable restrictions are difficult to work with and are generally unreliable for calibrating to a particular flow rate. Variable restrictors can also impede the collection efficiency of the analyte or may cause problems of chemical "carryover" or "memory," resulting from the retention of the analyte by the restriction.

As a specific example where different sampling requirements exist, sampling of air for the concentration of various chemical-warfare agents requires air sample volumes that are different for certain of the agents. Three such chemical-warfare agents are: (1) HD, a designation used for bis-(2-chloroethyl) sulfide, a blister agent commonly known as mustard gas; (2) GB, a designation used for isopropyl methylphosphonofluoridate, a nerve agent commonly known as sarin; and (3) VX, a designation used for O-ethyl S-[2-(diisopropylamino) ethyl] methylphosphonothiolate, another nerve agent. Monitoring for the agents HD, GB and VX typically requires sampling of different volumes of air for each agent. To determine the concentration of each agent, an air sample is pulled through the inlet of a chemical monitor such as the MIMCAMS, which is a miniature gas-chromatographic system manufactured and sold by CMS Field Products ("CMS") of O.I. Analytical. MINI-CAMS can be configured with one of several different gas-chromatographic detectors, such as a flame-ionization detector, a photoionization detector, a flame-photometric detector, or another detector that is sensitive to the volatile organic compounds of interest.

During the sampling portion of the MINICAMS monitoring cycle, air is pulled into the inlet of the MINICAMS through a preconcentrator tube containing a sorbent which traps the compounds of interest. The sample line is typically ¼-inch Teflon tubing having a length of 100 feet or more. Knowing the total volume of the air accurately is critical because the compound concentration must be based on the measurement of the amount of the compound trapped on the sorbent in relation to the total air sample volume.

Further complicating the monitoring of these agents, HD or GB propagate down the sample line and can be directly sampled, but agent VX must be chemically converted to its G-analog at the remote sample point before the G-analog propagates down the sample line and its concentration is determined. This conversion is necessary because VX has a very low vapor pressure and is difficult to transport through the sampling line. Converting agent VX to the G-analog, which is similar to nerve agents such as GB, is achieved by pulling the sampled air through a V-to-G conversion filter, or pad, impregnated with silver fluoride (AgF), which reacts with any VX present in the air sample to form the G-analog. The filter or pad is at the remote (distal) end of the sample line. The concentration of VX is proportional to the concentration of the G-analog. Although agent GB will pass through the conversion filter or pad, agent HD will not. Therefore, it is not possible to simultaneously sample agent HD and agent VX through the same sample line.

SUMMARY OF THE INVENTION

This invention solves the above problems and disadvantages by providing an apparatus for controllably varying the sample volume for each of two or more sample lines used with air monitoring equipment. The invention can sample different volumes of air from different sampling points by varying the sampling time at each point. The sample volume is varied depending on the compound or compounds of interest sampled through each line. To vary the volumes, time values are set or programmed by the operator to switch valves based on desired monitoring levels for different target analytes and the relative sensitivities of the monitoring system to detect the target analytes. The invention also can be used to sample sequentially from different points for different periods of time.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF A PREFERRED EMBODIMENT

Figure 1:
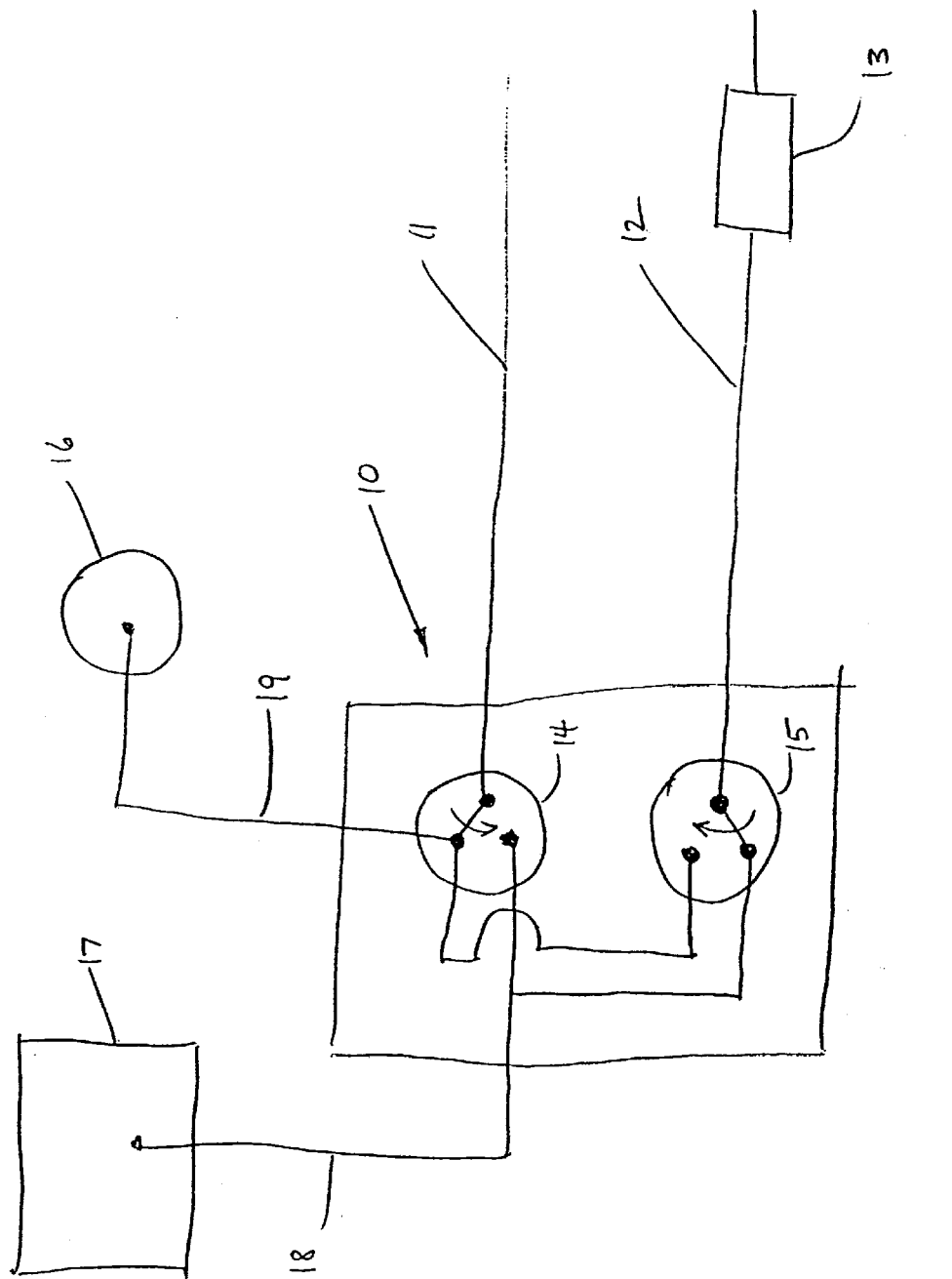
FIG. 1 is a schematic representation of the invention according to a preferred embodiment.

As shown in FIG. 1, Variable Split Sampler ("VSS") 10 is connected to sample lines 11 and 12. The preferred embodiment describes the use of the invention with two sample lines, but the invention also may be used with more than two sample lines at the same or multiple sampling points. As shown in FIG. 1, sample line 12 includes conversion filter or pad 13, which is used to convert agent VX to its G-analog. However, the present invention is typically used without flow restrictions in the sample lines, and therein lies the advantages of the invention, as will be described more fully herein. It is possible that the sample lines may include intended or unintended flow restrictions therein. As will be understood by those skilled in the art, filter or pad 13 is an example of a flow restriction that restricts the flow rate through sample line 12. The VSS can be used in conjunction with a gas flow controller to easily and automatically compensate for different sample line restrictions while still varying the relative volumes of air sampled through the two lines.

In a preferred embodiment, the VSS includes control valves 14 and 15 that are used to select one of the sample lines to be sampled by monitoring system 17 through line 18. The control valves in a preferred embodiment are electrically actuated, although pneumatically actuated control valves also may be used. When one sample line is being directed to the monitoring system, the second line is directed through line 19 to bypass pump 16.

Monitoring system 17 (e.g., MINICAMS system) typically includes a vacuum source (pump) and a standard gas flow controller that measures and controls the flow rate through whichever of the two sample lines is directed to the monitor by the VSS. The use of a flow controller with the VSS automatically compensates for differences in sample line restrictions. The flow controller regulates the air flow to a set amount by sensing the air flow and adjusting an electronically variable restriction such that the air flow is the specified amount. If different restrictions exist in each of the two sample lines, the flow controller adjusts the restriction such that the sample flow through each of the two sample lines is the desired flow.

To select the sample volumes for each of the two sample lines, the operator programs the VSS to switch control valves 14 and 15 at certain times in the monitoring cycle to achieve the desired sampling time for each line. The two lines are sampled sequentially and repetitively. In this way, different and reproducible sample volumes can be collected for each of the two sample lines. For example, if it is desired that 20% of the air volume that is sampled be from one sample line (i.e., the HD path) and 80% from the second sample line (i.e., the VX path), then the valves are timed such that 20% of the time the first path is enabled and 80% of the time the second path is enabled.

In a preferred embodiment, the operator programs the VSS to switch the control valves according to the desired proportion of flows from each sample line. This programming is done by setting a potentiometer or switch as will be described in more detail below. The flow volume from each sample line to the sampling device is determined and controlled by proportional time the valve is open for that sampling line. Accordingly, the present invention allows the relative sampling time to be accurately set to collect different sample volumes for two sample lines.

Figure 2:
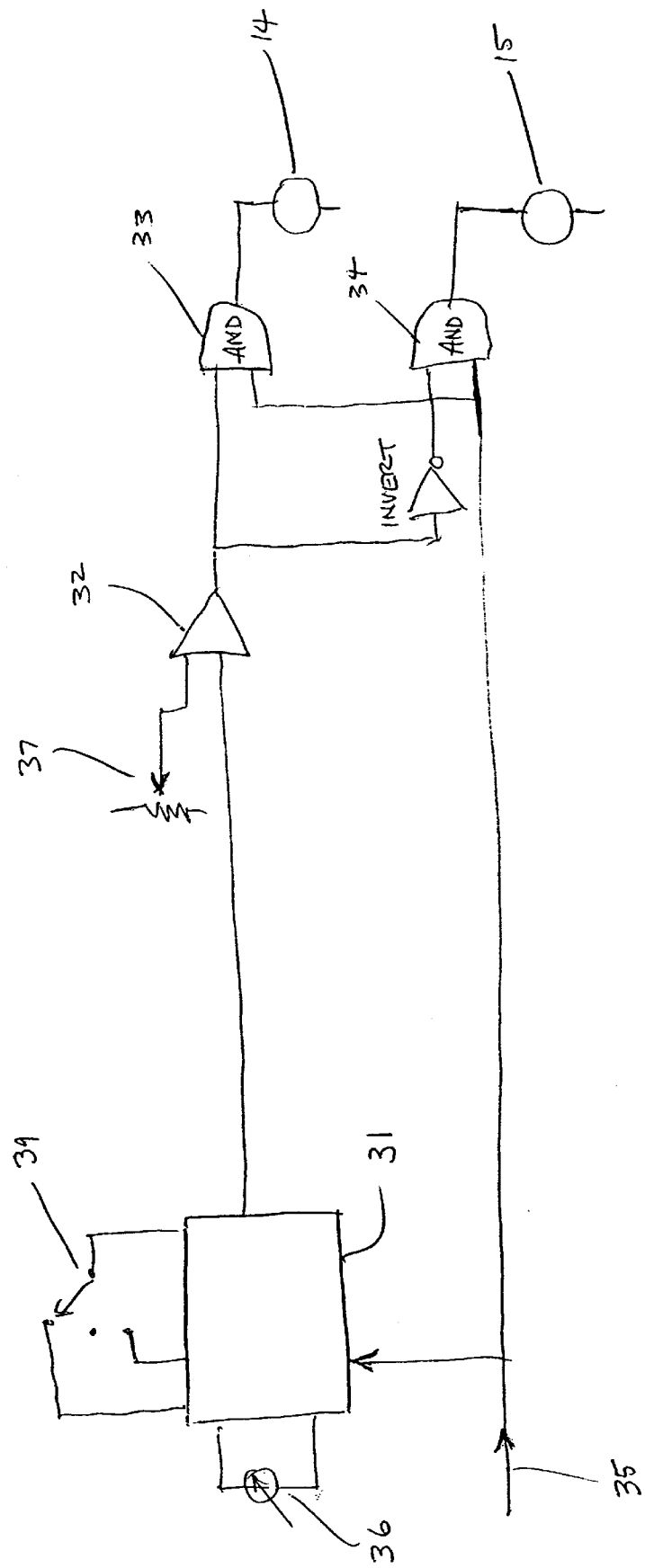
FIG. 2 is a schematic of the electronics used in a preferred embodiment of the present invention.

A preferred embodiment showing an analog implementation of the control valves used in the present invention is shown in FIG. 2. The device of the present invention includes an electronic timing generator that may be implemented in a digital or analog configuration. As shown in FIG. 2, in a preferred embodiment control valves 14 and 15 are timed and controlled by gated adjustable frequency triangle wave oscillator 31, adjustable level comparator 32, and valve drivers 33 and 34. Alternatively, other adjustable frequency timing generators also may be used in accordance with the principles of the present invention, instead of the oscillator and comparator shown in the preferred embodiment.

Operation of the control valves according to the analog implementation of a preferred embodiment is as follows. When gate signal 35 from air monitor 17 is in the enabled state, the timing generator (here shown as adjustable frequency triangle wave oscillator 31) produces a sequence of actuation signals to control valves 14 and 15 such that only a single valve is actuated at any given time. In a preferred embodiment, the adjustable frequency triangle wave oscillator produces periodic linear rising and falling voltage known as a triangle wave. An adjustment control sets the frequency and may be adjusted to a desired frequency. In a preferred embodiment, the adjustment control is adjustment potentiometer 36 that sets the frequency of oscillation. Another adjustment control sets the proportion of time that each control valve is actuated during each cycle of the periodic sequence, and may be adjusted by the operator to a desired proportion of time. In a preferred embodiment, the adjustment control is adjustable level comparator 32 which converts the triangle wave from the oscillator to a proportional time logical state. The output of the comparator goes to a logic "1" state when the triangle wave voltage rises above an adjustable threshold voltage referred to as proportional time adjust 37. The threshold voltage may be adjusted by the operator, to control the proportion of time that the comparator output is in a logic "1" or logic "0" state during each triangle wave cycle.

In a preferred embodiment, the comparator is connected to valve drivers 33 and 34 which convert the logical state to actuation current through valves 14 and 15. In a preferred embodiment, each of the valve drivers use AND gate logic. The logic state of the comparator output is directly applied to first valve driver 33, but is inverted prior to application to second valve driver 34. In this manner, only one valve driver logic is driven at any given time. When driven, each valve driver applies actuation current to the respective valve coil of the specified electrically actuated control valve.

When gate signal 35 is in the disabled state, neither control valve is actuated. In a preferred embodiment, the driver logic circuits are disabled such that neither valve is actuated. During this time, the valves route both sample streams to bypass 19.

In a preferred embodiment, three position mode switch 39 is used for calibration. The center position is the normal "operate" position and the other positions cause either valve 14 or valve 15 to be continuously actuated. In the embodiment of FIG. 2, setting the mode switch in either of the other positions overrides the triangle wave oscillator and forces the output voltage to be continuously either at the high level or low level voltage. The comparator output will then be continuously in either the logic "1" or logic "0" state. The appropriate valve driver logic will be continuously driven and the appropriate control valve will be continuously actuated. In this state a specified amount of calibration compound can be injected into the selected stream and all of the injected amount will be routed to the air monitoring system.

Although variations in the embodiment of the present invention may not each realize all of the advantages of the invention, certain features may become more important than others in various applications of the device. The invention, accordingly, should be understood to be limited only by the scope of the appended claims.

What is claimed is:

1. A device comprising:
   (a) at least two sample lines connected between a sample point and an air monitor; a converter in at least one sample line to convert a first chemical compound to a second chemical compound that is absent in at least one other sample line;
   (b) a plurality of control valves, each of the control valves between a sample line and the air monitoring device;
   (c) a timing generator for providing repeated on-off signals to each valve during a sampling time period, each on-off signal causing one valve to open and the other valves to close; and
   (d) a timing adjuster connected to the timing generator to ensure that the on-off signals from the timing generator to the valves are provided to open each valve for a proportion of the total sampling time period correlating to the proportion of the total sample volume to be collected from the sample line connected through that valve.

2. The device of claim 1 wherein the frequency of the timing generator is adjustable.

3. The device of claim 1 wherein the timing of on-off signals is adjustable.

4. The device of claim 1 further comprising a bypass pump that is connected to each of the valves for directing flow from each sample line when the valve in that line is closed.

5. The device of claim 1 further comprising a flow controller connected to the air monitor to regulate the flow rate in each sample line.

6. A device for selecting and adjusting the volume of air sampled through each sample line connected to air monitoring equipment, comprising:
   (a) at least one sample line to convert specified chemical compounds therein through a flow restriction;
   (b) a valve in each sample line, each valve having a first position for directing flow to the air monitoring device and a second position for directing flow to a bypass; and
   (c) an electrical timer connected to each of the valves, the electrical timer directing timing signals to the valves, the timing signals causing one of the valves to be in the first position when the other valve is in the second position, the electrical timer including an adjustment for varying the fraction of a specified total sampling time period when each valve is to be in the first position, the fraction corresponding to the proportion of total sample volume to be collected from the sample line for each valve.

7. The device of claim 6 wherein the electrical timer is an oscillator and a comparator.

8. The device of claim 6 wherein the air monitoring device includes a gas flow controller.

9. A device for selecting and adjusting the volume of air sampled through each sample line connected to air monitoring equipment, comprising:
   (a) a conversion filter in at least one sample line to convert specified chemical compounds therein; the same conversion filter being absent from at least one other sample line;
   (b) a valve in each sample line, each valve having a first position to direct flow to the air monitoring device and a second position to direct flow to a bypass; and
   (c) an electrical timer connected to each of the valves, the electrical timer directing timing signals to the valves, the timing signals causing one of the valves to be in the first position when the other valve is in the second position, the electrical timer including an adjustment to vary the fraction of a specified total sampling time period when each valve is to be in the first position, the fraction corresponding to the proportion of total sample volume to be collected from that sample line.

* * * * *